United States Patent [19]

Asher et al.

[11] Patent Number: 5,084,049

[45] Date of Patent: Jan. 28, 1992

[54] TRANSVERSE CONNECTOR FOR SPINAL COLUMN CORRECTIVE DEVICES

[75] Inventors: Marc Asher, Prairie Village, Kans.; Walter E. Strippgen, Golden, Colo.; Charles Heinig, Charlotte, N.C.; William Carson, Columbia, Mo.

[73] Assignee: AcroMed Corporation, Cleveland, Ohio

[21] Appl. No.: 308,433

[22] Filed: Feb. 8, 1989

[51] Int. Cl.$^5$ ............................................. A61F 5/04
[52] U.S. Cl. ........................................ 606/61; 606/60; 606/73; 128/69
[58] Field of Search ................. 128/69; 606/60, 61, 606/72, 73; 623/16, 17

[56] References Cited

U.S. PATENT DOCUMENTS

| | | | |
|---|---|---|---|
| 3,648,691 | 3/1972 | Lumb et al. | 128/69 X |
| 3,693,616 | 9/1972 | Roaf et al. | |
| 4,112,935 | 9/1978 | Latypov et al. | |
| 4,269,178 | 5/1981 | Keene | |
| 4,361,141 | 11/1982 | Tanner | |
| 4,411,259 | 10/1983 | Drummond | |
| 4,433,677 | 2/1984 | Ulrich et al. | 128/69 |
| 4,448,191 | 5/1984 | Rodnyansky et al. | 128/69 |
| 4,611,581 | 9/1986 | Steffee | 128/69 |
| 4,641,636 | 2/1987 | Cotrel | |
| 4,815,453 | 3/1989 | Cotrel | |

FOREIGN PATENT DOCUMENTS

| | | |
|---|---|---|
| 0283373 | 3/1988 | European Pat. Off. |
| 0284530 | 3/1988 | European Pat. Off. |
| 0301489 | 7/1988 | European Pat. Off. |
| 2928216 | 1/1981 | Fed. Rep. of Germany |
| 2506606 | 5/1982 | France |
| 2612070 | 9/1988 | France |
| 1-121046 | 3/1989 | Japan |
| 1063404 | 12/1983 | U.S.S.R. ............................. 128/69 |
| 780652 | 8/1957 | United Kingdom ................. 128/69 |

OTHER PUBLICATIONS

Product Encyclopedia, Zimmer-U.S.A., Inc., 1978, pp. B203 & B204, "Knodt distraction-fusion instrumentation".
Zimmer Catalog-Warsaw, Indiana, 46580, 1973, p. D67, Fig. 10.
Danek Medical Catalogue-Discloses a cross connector between rods for supporting vertebrae.

Primary Examiner—Richard J. Apley
Assistant Examiner—Linda C. M. Dvorak
Attorney, Agent, or Firm—Tarolli, Sundheim & Covell

[57] ABSTRACT

An apparatus comprising a pair of corrective devices for a spinal column. A member is extendable between the corrective devices in a direction transverse to the longitudinal central axes of the corrective devices. A first portion of the member is connected with one of the corrective devices and a second portion of the member is connected with the other of the corrective devices. The locations at which the corrective devices are connected with the member may be changed to enable the member to interconnect the corrective devices spaced different distances apart and at different orientations.

25 Claims, 12 Drawing Sheets

TRANSVERSE CONNECTOR FOR SPINAL COLUMN CORRECTIVE DEVICES

BACKGROUND OF THE INVENTION

1. Technical Field

The present invention relates to a transverse connector for interconnecting spinal column corrective devices and, in particular, to a transverse connector which enables the spacing of the corrective devices at different distances apart and at different orientations.

2. Description of the Prior Art

Transverse connectors for interconnecting spinal column corrective devices are known. U.S. Pat. No. 3,693,616 discloses a pair of bars for correcting curves of the spinal column. Each of the bars have a plurality of openings extending therethrough. The bars are located on opposite sides of the spinous processes and are connected to the spinal column by a lacing wire extending through the openings around portions of the spinal column Spacers are located between the bars and each spacer has axial end portions connected with the bars to block relative movement of the bars.

Transverse connectors for interconnecting a pair of rods which are connectable with the spinal column are also known. One such transverse connector, referred to as a "Transverse Fixator", includes a pair of clamp halves. A pair of spaced apart recesses are located in each of the clamp halves at a fixed distance apart. The clamp halves cooperate so facing recesses receive a portion of one of the rods therebetween. A fastener is inserted through an opening in one clamp half and is tightened in a threaded opening in the other clamp half. The clamp halves, thus, grip around respective portions of the rods and block relative movement of the rods.

Another transverse connector for rods, available from Stuart in Greensburg, Pennsylvania, includes an elongate threaded rod with a pair of clamps. A clamp half of one of the clamps is fixed to an end of the threaded rod. The other clamp half of the one clamp is movable along the threaded rod toward the fixed clamp half to grip around a portion of a corrective rod. Another one of the clamps grips around a portion of the another corrective rod and is movable along the threaded rod to allow the corrective rods to be spaced apart at different distances.

Another such transverse connector for rods, available from Danek in Memphis, Tennessee, includes a plate having a pair of rectangular openings. The plate also has a pair of parallel extending recesses located at a fixed distance apart for receiving a portion of respective rods. An eyebolt is received on a portion of a rod and is received in the rectangular opening in the plate. When a nut is tightened on the eyebolt, the rods are drawn into the recesses to clamp the rods and block relative movement of the rods.

SUMMARY OF THE INVENTION

The present invention is directed to a transverse connector for interconnecting a pair of members, such as spine plates or rods, which are connectable with vertebrae of a spinal column. Each spine plate has a plurality of openings for receiving a fastener to connect the spine plate to a vertebra. The transverse connector comprises a member extendable between the spine plates in a direction transverse to the axes of the openings in the spine plates. First attaching means connects a first portion of the member with one of the spine plates. Second attaching means connects a second portion of the member with the other of the spine plates. The locations of the first and second attaching means along the member may be changed to enable the member to interconnect the spine plates which can be spaced different distances apart.

In one embodiment of the present invention, the member comprises an elongate plate with an elongate opening Each of the first and second attaching means comprises a fastener which attaches the elongate plate to a spine plate and includes a portion extendable through the elongate opening in the elongate plate and through an opening in the spine plate. The fastener is movable along the length of the elongate opening in the elongate plate to change the location at which the fastener attaches the spine plate to the elongate plate.

In another embodiment, the member comprises an elongate rod having threaded axial end portions. Each of the first and second attaching means comprises a clamp connectable with a respective threaded end portion of the rod. Each clamp includes a first portion receivable in an opening in one of the spine plates. A second portion of the clamp cooperates with the first portion to apply a clamping force to a portion of the spine plate. Each of the clamps are movable along the rod to change the location at which the clamps attach the spine plates to the rod.

In yet another embodiment, the member comprises an elongate rod having end portions which are threaded. Each of the first and second attaching means comprises a clamp. Each clamp includes a portion with an internally threaded opening for threaded engagement with one of the threaded end portions of the rod. Each portion of each clamp is movable axially along the rod in response to rotation of the rod about its longitudinal central axis.

In still another embodiment of the present invention, the transverse connector interconnects a pair of corrective rods each of which are connectable with vertebrae of a spinal column. The transverse connector comprises an elongate rod extendable between the corrective rods in a direction transverse to the longitudinal central axes of the corrective rods. The elongate rod has end portions which are threaded in opposite directions. Each of a pair of clamps is connectable with a respective threaded end portion of the elongate rod. Each clamp includes a first portion and a second portion cooperating with the first portion to apply a clamping force to a portion of one of the corrective rods. The first portions are moved relatively toward one another in response to rotation of the rod about its longitudinal central axis in a first direction. The first portions are moved relatively away from one another in response to rotation of the rod about its longitudinal central axis in a second direction opposite the first direction.

In yet another embodiment of the present invention, an articulated transverse connector is used to interconnect skewed spine rods. The articulated transverse connector includes first and second connecting members, each of which have an axial end portion and a longitudinal central axis. Clamp means attaches the connecting members to the spine rods. The axial end portions of the connecting members are connected by a joint capable of articulation so the connecting members may be positioned with their longitudinal central axes skewed relative to one another.

DESCRIPTION OF THE DRAWINGS

Further features of the present invention will become apparent to those skilled in the art to which the present invention relates from reading the following specification with reference to the accompanying drawings, in which.

DESCRIPTION OF SPECIFIC PREFERRED EMBODIMENTS

Figure 1:
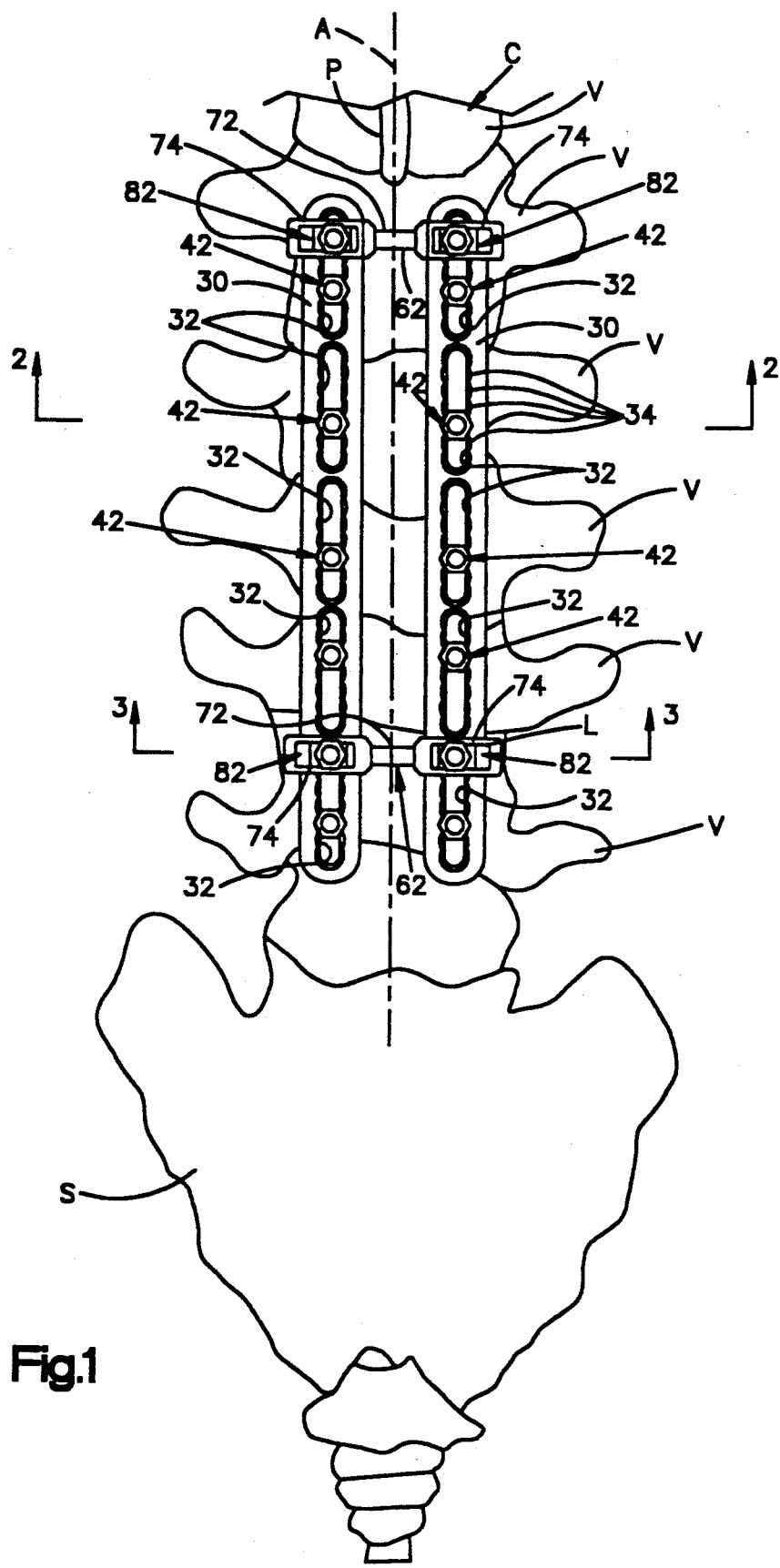
FIG. 1 is a view of one embodiment of the transverse connector of the present invention interconnecting a pair of spine plates which are connected to a spinal column.

One embodiment of the present invention is illustrated in FIG. 1. A portion of a spinal column C (FIG. 1) includes a plurality of vertebrae V and a sacrum S. A pair of spine plates 30 are connected to some of the vertebrae V to maintain the relative positions of the vertebrae. The spinous process P of each vertebra may be removed if required. It will be apparent that the spine plates 30 may be located anywhere along the spinal column C, and the location of the spine plates illustrated in FIG. 1 is for example purposes.

Figure 2:
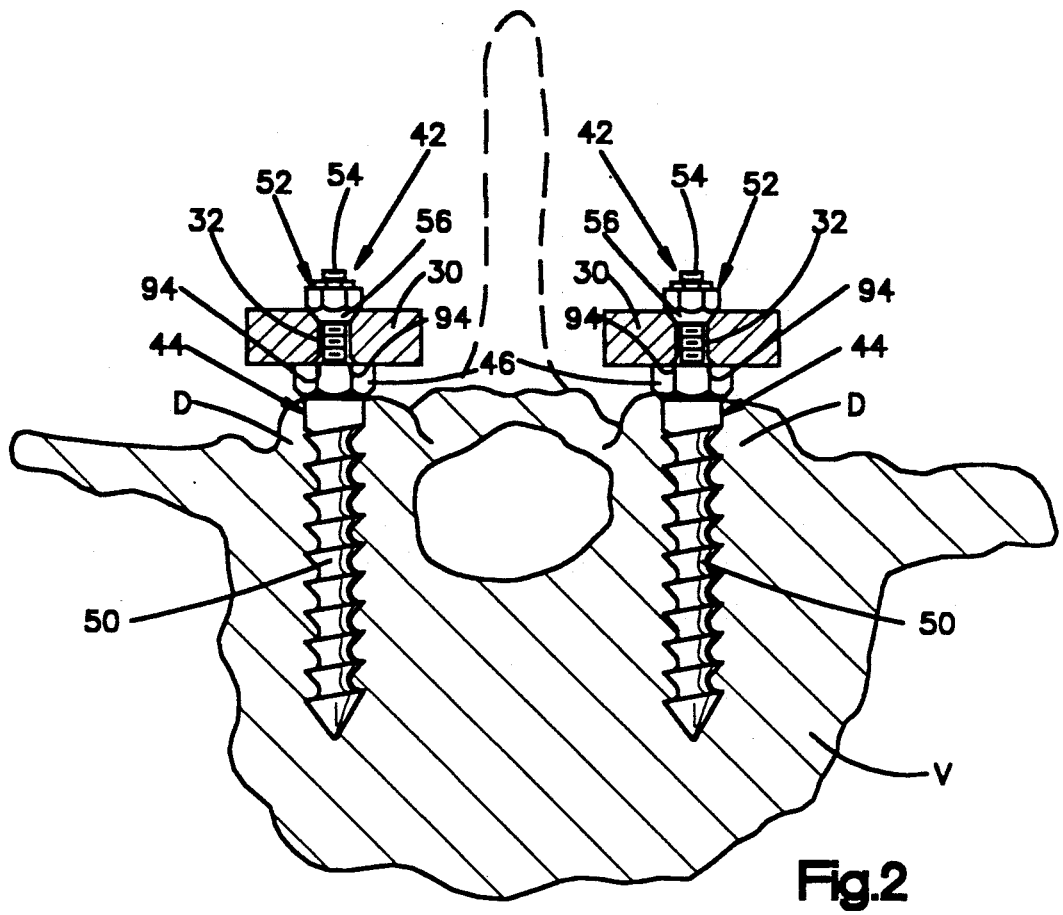
FIG. 2 is an enlarged cross sectional view of the spine plates in FIG. 1 connected to a vertebra, taken approximately along line 2—2 in FIG. 1.

Each of the spine plates 30 is elongate and has a sufficient length to span several vertebrae V. A plurality of elongate openings 32 extend through each spine plate 30. The openings 32 receive a fastener 42, as illustrated in FIG. 2, to connect each of the spine plates to a pedicle D of the vertebra V. A plurality of frustoconical or semi-spherical shaped recesses 34 are spaced along the length of each opening 32.

Each fastener 42 includes a bone screw 44 (FIG. 2) having a threaded portion 50 threaded into a cancellous portion of the vertebra V. A shoulder 46 on the screw 44 spaces the spine plate 30 away from vertebra V. The fastener 42 also includes a nut 52 which is threaded onto another threaded portion 54 of the screw 44 which extends through the opening 32. The nut 52 is received in one of the recesses 34 spaced along the opening 32. The nut 52 has an external portion 56 for engaging the surface of a recess 34 to block movement of the spine plate 30 relative to the screw 44.

Figure 3:
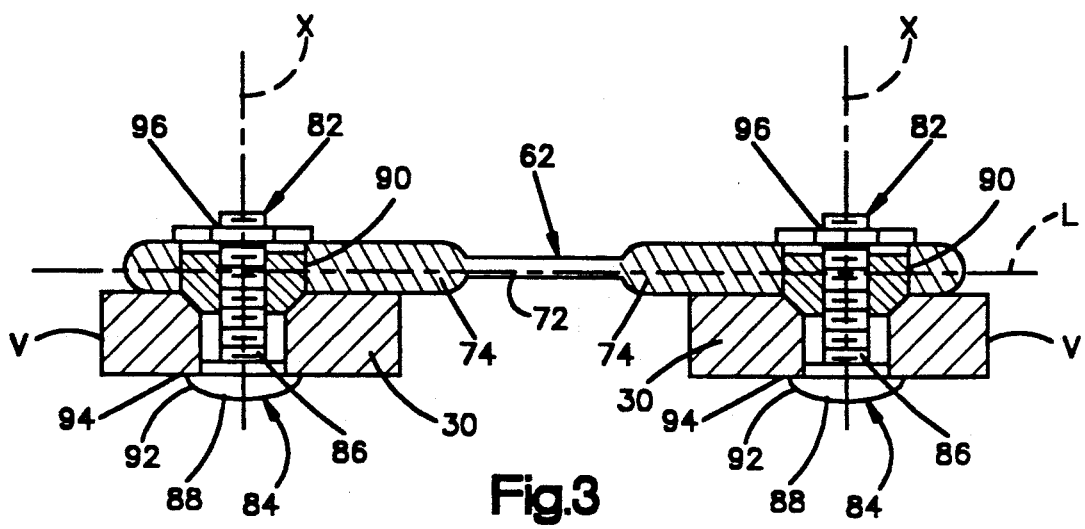
FIG. 3 is an enlarged cross sectional view of the transverse connector in FIG. 1 interconnecting the spine plates, taken approximately along line 3—3 in FIG. 1.

A pair of transverse connectors 62 (FIGS. 1 and 3) interconnect the spine plates 30. The transverse connectors 62 block relative movement of the spine plates 30 so the vertebrae V connected to the spine plates are maintained in their desired relative positions and do not pivot relative to an anterior-posterior axis or a longitudinal central axis A of the spinal column C. The transverse connectors 62 are located near axially opposite end portions of the spine plates 30 so the resulting structure forms a parallelogram. It will be apparent that the transverse connectors 62 may be located anywhere along the elongate openings 32 of the spine plates 30.

Each transverse connector 62 (FIG. 3) includes a pair of elongate plate portions 74 to connect together the spine plates 30. The plate portions 74 extend transversely to the axes X of the openings 32 in the spine plates 30 and are connected by a bendable rod portion 72. Each plate portion 74 includes a pair of elongate openings which extend in a direction substantially parallel to and along the longitudinal central axis L of the connector 62. The rod portion 72 may be bent to allow the plate portions 74 to be located flat against a respective spine plate 30 to accommodate non-coplanar and-/or non-parallel spine plates 30.

Figure 3A:
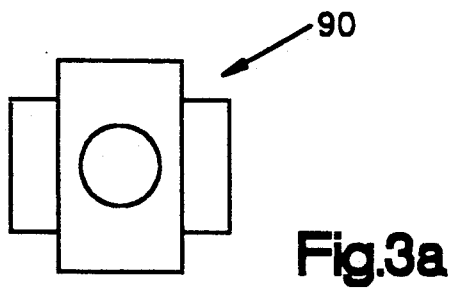
FIG. 3a is an enlarged view of a cross bracket in FIG. 3.
Figure 3B:
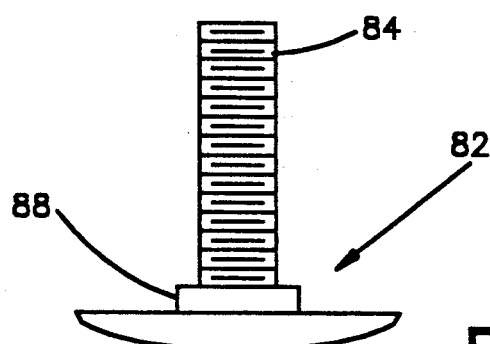
FIGS. 3b and 3c are enlarged view of a fastener in FIG. 3.
Figure 3C:
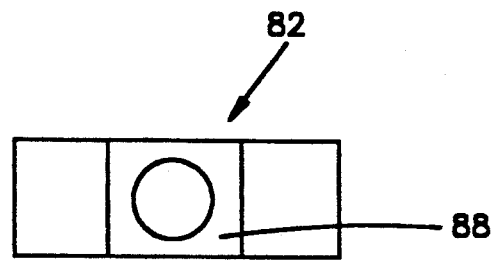

A fastener 82 (FIG. 3b) extends through a respective opening to connect one of the plate portions 74 with one of the spine plates 30. The fastener 82 includes a screw 84 having a threaded portion 86 extending through a cross bracket 90 (FIG. 3a) located in the opening 32 in the spine plate 30 and through the opening in the plate portion 74. The screw 84 also includes a square head 88 (FIG. 3c) which fits in the opening (best seen in FIG. 3) in a surface of the spine plate 30. The square head 88 interacts with the opening to block rotation of the screw 84 about its longitudinal central axis during tightening of a nut 96 onto the screw. The cross bracket 90 blocks the transverse connector 62 from pivoting about the axis X relative to the spine plate 30.

The nut 96 includes an internally threaded opening for threaded engagement with the threaded portion 86 of the screw 84. The nut 96 also includes a hex head for receiving a tool, such as a wrench, to tighten the nut onto the screw 84. When the nut 96 is sufficiently tightened against the plate portion 74, a clamping force is applied between the plate portion 74 and the spine plate 30 to block relative movement therebetween.

The spine plates 30 may be spaced different distances apart to accommodate different size vertebrae V or location requirements determined by the surgeon attaching the spine plates. In order to permit one design of the transverse connector 62 to be used with the spine plates 30 spaced apart at different distances, the fastener 82 may be located at different positions along the opening in the plate portion 74. For example, if the spine plates 30 were located at different distances apart from the position illustrated in FIG. 3, the threaded portion 86 of each fastener 82 could be relocated along the openings in the plate portion 74. Thus, an assortment of different length transverse connectors or transverse connectors having different distances between openings for receiving the fasteners 82 is unnecessary.

Figure 4:
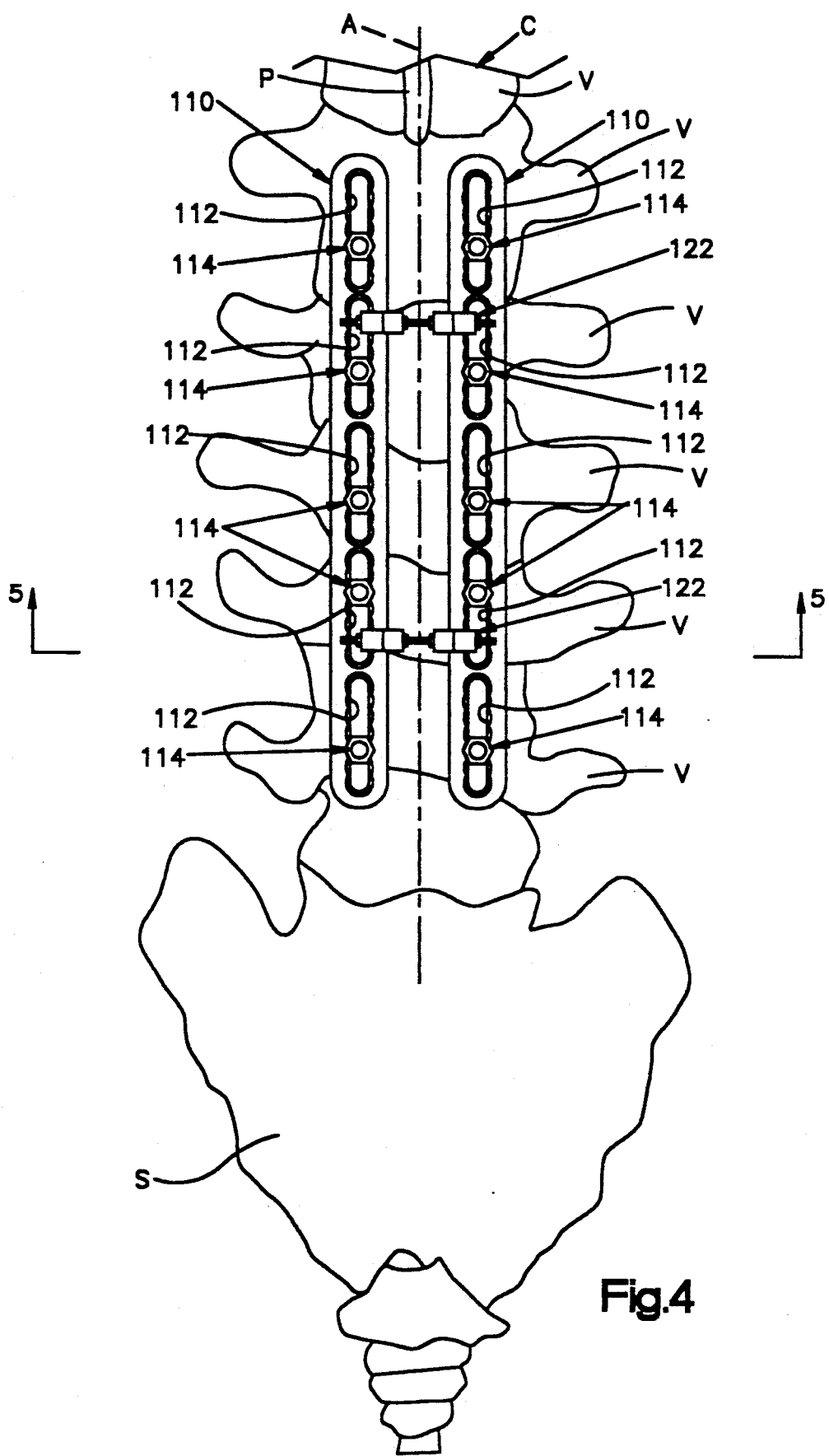
FIGS. 4, 6, 10, 13, 15 and 17 are views similar to FIG. 1 illustrating other embodiments of the transverse connector of the present invention.
Figure 5:
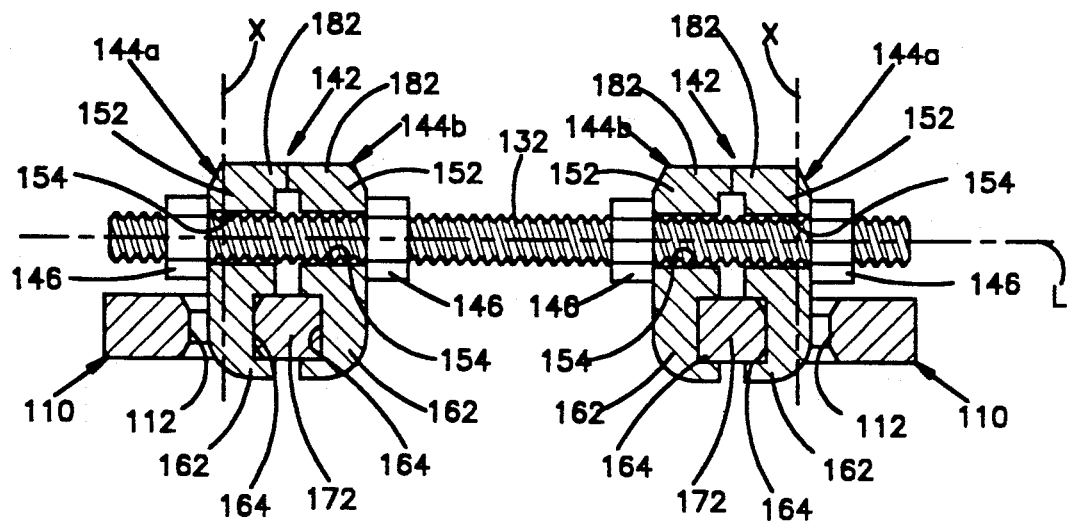
FIG. 5 is an enlarged cross sectional view of the transverse connector in FIG. 4 interconnecting the spine plates, taken approximately along line 5—5 in FIG. 4.

Another embodiment of the transverse connector of the present invention is illustrated in FIGS. 4 and 5. Spine plates 110 are connected to vertebrae V of the spinal column C. Each spine plate 110 has a plurality of elongate openings 112 which receive fasteners 114 to connect the spine plates to the vertebrae V, as described above. A pair of transverse connectors 122 interconnect the spine plates 110 to block relative movement between the spine plates.

Each transverse connector 122 (FIG. 5) includes an elongate threaded rod 132 extending between the spine plates 110 in a direction transversely to the axes X of the openings 112 in the spine plates 110. A pair of axially spaced clamps 142 attach the rod 132 to the spine plates 110. The threaded rod 132 may be bent if necessary to accommodate non-coplanar and/or non-parallel spine plates 110.

Each clamp 142 includes a pair of similar clamp halves 144 which clamp around a portion of one of the spine plates 110. A pair of nuts 146 are located on opposite sides of the clamp 142. The clamp halves 144 are pressed together to clamp the spine plate 110 when the nuts 146 are rotated on the rod 132 in a direction toward one another.

Each clamp half 144 includes a connector portion 152. An opening 154 extends through the connector portion 152 and receives a portion of the rod 132. The inner diameter of the opening 154 is sized larger than the crest diameter of the thread on the rod 132. The clearance created allows the clamp half 144 to rest squarely on the spine plate 110.

Each clamp half 144 also includes a body portion 162 extending from the connector portion 152. The body portion 162 includes a surface defining a rectangular recess 164. The body portion 162 of one clamp half 144a extends into the opening 112 in the spine plate 110. The other clamp half 144b cooperates with the clamp half 144a received in the opening, to apply a clamping force to a rectangular portion 172 of the spine plate 110 received between the clamp halves. The rectangular recesses 164 in clamp halves 144a, 144b define a rectangular opening which is slightly larger than the rectangular portion 172 of the spine plate. Thus, little or no relative rotation between the spine plate 110 and clamp 142 occurs in a plane containing the longitudinal central axis L of the rod 132 and which extends substantially perpendicular to the spine plate 110.

A spacer portion 182 extends from the connector portion 152 of each clamp half 144 on an opposite side of the opening 154 than the body portion 162. When the clamp halves 144a, 144b are moved toward one another, the spacer portions 182 on each clamp half engage one another. As the clamp halves 144a, 144b are pressed together by the nuts 146 being tightened on the rod 132, the body portions 162 pivot toward one another about the spacer portions 182, so the clamping force is transmitted to the body portions 162 to grip the portion 172 of the spine plate 110.

Figure 7:
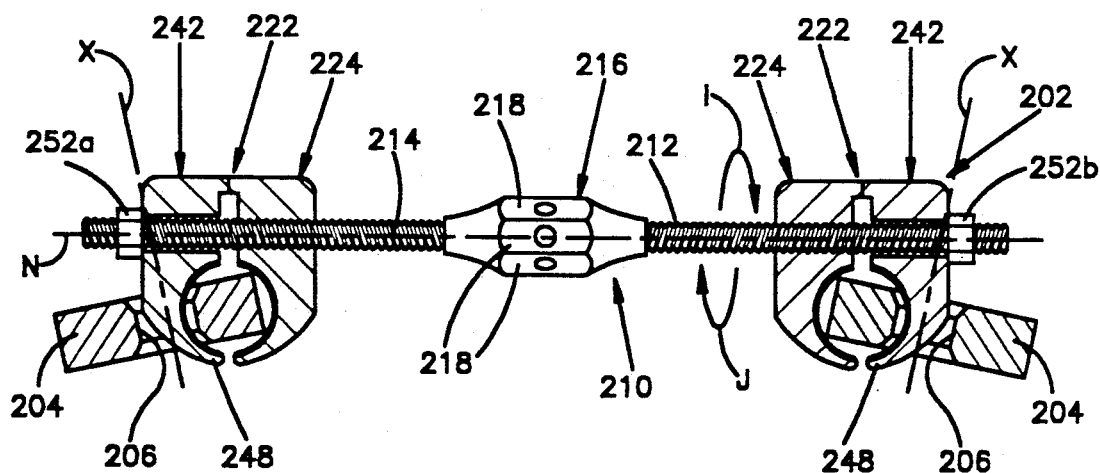
FIG. 7 is an enlarged cross sectional view of the transverse connector in FIG. 6 interconnecting the spine plates, taken approximately along line 7—7 in FIG. 6.
Figure 6:
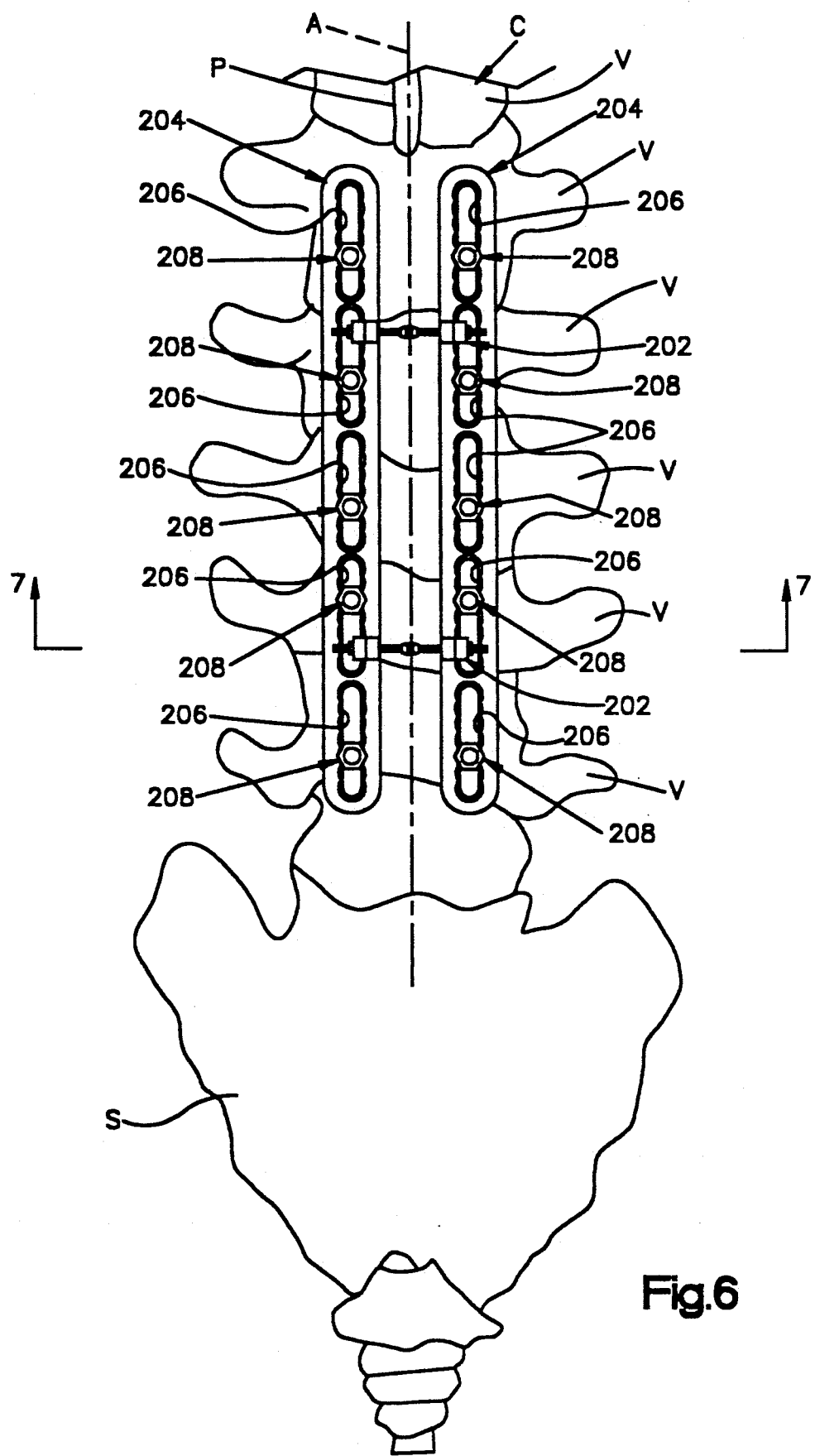

Another embodiment of the transverse connector of the present invention is illustrated in FIGS. 6 and 7. The transverse connector 202 (FIGS. 6 and 7) interconnects a pair of spine plates 204. The transverse connector 202 may be used when the spine plates 204 are skewed relative to one another, as illustrated in FIG. 7. Each spine plate 204 has a plurality of openings 206 for receiving a fastener 208 to connect the spine plate to a vertebra V, as described above.

The transverse connector 202 (FIG. 7) includes an elongate member 210 having an axial end portion 212 with a righthand thread and an axial end portion 214 with a lefthand thread. A drive portion 216 is located intermediate the threaded axial end portions 212, 214. The drive portion 216 receives a suitable tool (not shown) for applying a torque to the member 210 and rotating the member about its longitudinal central axis N in either direction. The drive portion 216 has a hexagonal shape taken in a plane extending perpendicular to the longitudinal central axis N of the member 210. The drive portion 216 includes diametrically opposite flats 218 which can be engaged by a wrench for rotating the member 210 or blocking rotation of the member. The drive portion 216 also includes an opening centrally located in each of the flats 218 for receiving a projection extending from a tool for rotating the member 210 or blocking rotation of the member.

Figure 8:
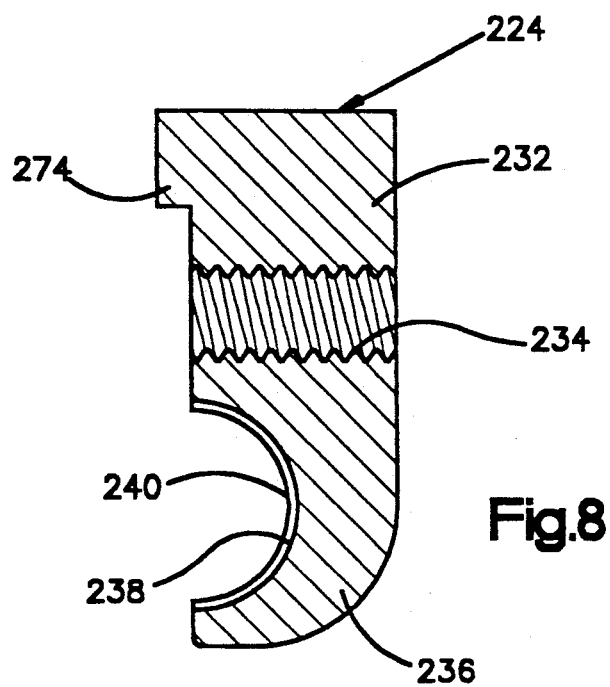
FIG. 8 is an enlarged cross sectional view of a portion of one of the clamps illustrated in FIG. 7.

The transverse connector 202 also includes a pair of clamps 222 for attaching the member 210 to the spine plates 204. Each of the clamps 222 includes an inner clamp half 224 (FIGS. 7 and 8). The inner clamp half 224 includes a body 232 with a threaded opening 234 (FIG. 8) extending therethrough for threaded engagement with one of the threaded end portions 212, 214 of the member 210. A body portion 236 extends from the connector portion 232 of the inner clamp half 224. The body portion 236 is machined to form an arcuate recess 238 with a pair (only one of which is shown in FIG. 8) of axially spaced arcuate surfaces 240.

The inner clamp half 224 for threaded engagement with the threaded end portion 212 has a righthand threaded opening 234. The inner clamp half 224 for threaded engagement with the threaded end portion 214 has a lefthand threaded opening 234. When the member 210 is rotated in one direction, as indicated by the arrow I in FIG. 7, about its longitudinal central axis, the inner clamp halves 224 are moved toward one another. When the member 210 is rotated about its longitudinal central axis in another opposite direction, as indicated by the arrow J in FIG. 7, the inner clamp halves 224 are moved axially along the member away from one another.

Figure 9:
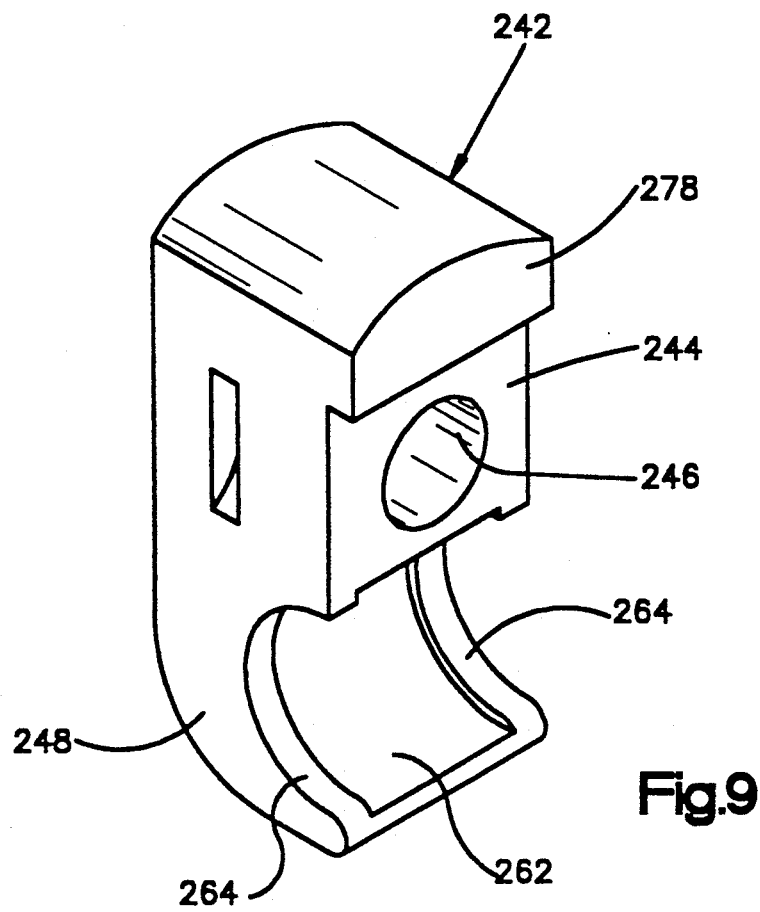
FIG. 9 is an enlarged perspective view of another portion of one of the clamps illustrated in FIG. 7.

Each of the clamps 222 also include an outer clamp half 242. Each outer clamp half 242 includes a connector portion 244, as illustrated in FIGS. 7 and 9, with an opening 246 extending therethrough for receiving a portion of the member 210. The outer clamp half 242 may be used on either of the threaded end portions 212, 214. A body portion 248 of the outermost clamp half 242 extends into an opening 206 in the spine plate 204. The body portion 236 of the inner clamp half 224 cooperates with the body portion 248 of the outer clamp half 242 to clamp around a portion of the spine plate 204.

After the inner clamp halves 224 have been moved to a position engaging the spine plates 204, each outer clamp half 242 is pressed against the respective inner clamp half 224 by rotating and tightening a nut 252a, 252b against the outer clamp half 242. The nut 252a has a lefthand threaded opening for threaded engagement with the threaded end portion 214 of the member 210. The nut 252b has a righthand threaded opening for threaded engagement with the threaded end portion 212 of the member 210. It will be apparent that the threaded clamp halves 224 may be located axially outwardly of the nonthreaded clamp halves 242 and the nuts 252a, 252b located axially inwardly of the nonthreaded clamp halves. It will also be apparent that a threaded rod similar to the threaded rod 132, described above, and having a constant thread along its length, may be used with clamp halves 224 with the same direction thread.

The clamp half 242 includes a recess 262 (FIG. 9) located between axially spaced arcuate surfaces 264. When the clamp halves 224, 242 are pressed together, the arcuate surfaces 240 and 264 engage the spine plate 204. Thus, each clamp 222 engages axially spaced portions of the spine plate 204. Such axially spaced surfaces on a clamp are disclosed in U.S. Patent application Ser. No. 308,430, now allowed entitled "Connector for a Corrective Device", in the name of Asher et al., filed concurrently with the present application, and assigned to the assignee of the present invention.

Figure 10:
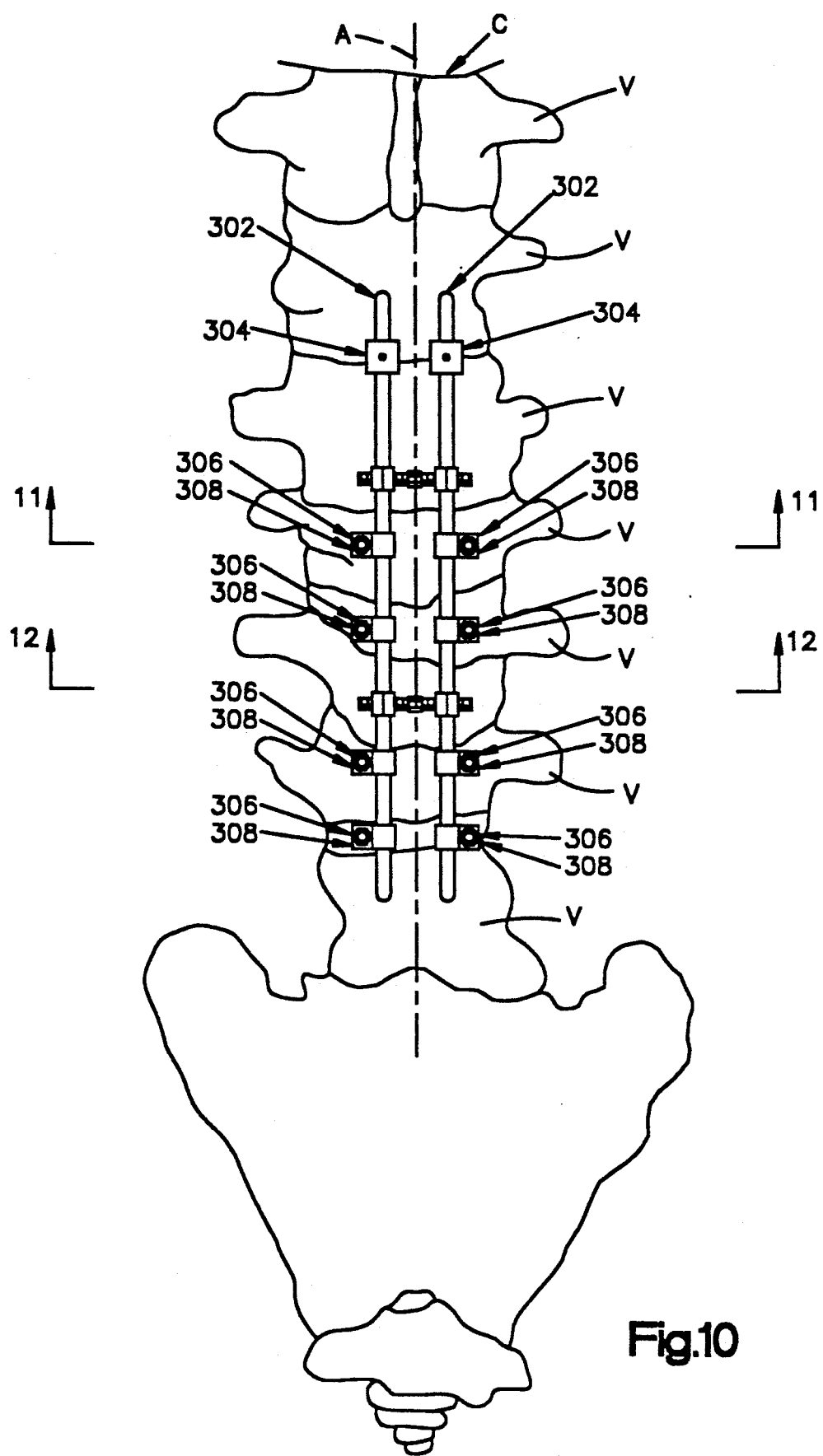
Figure 11:
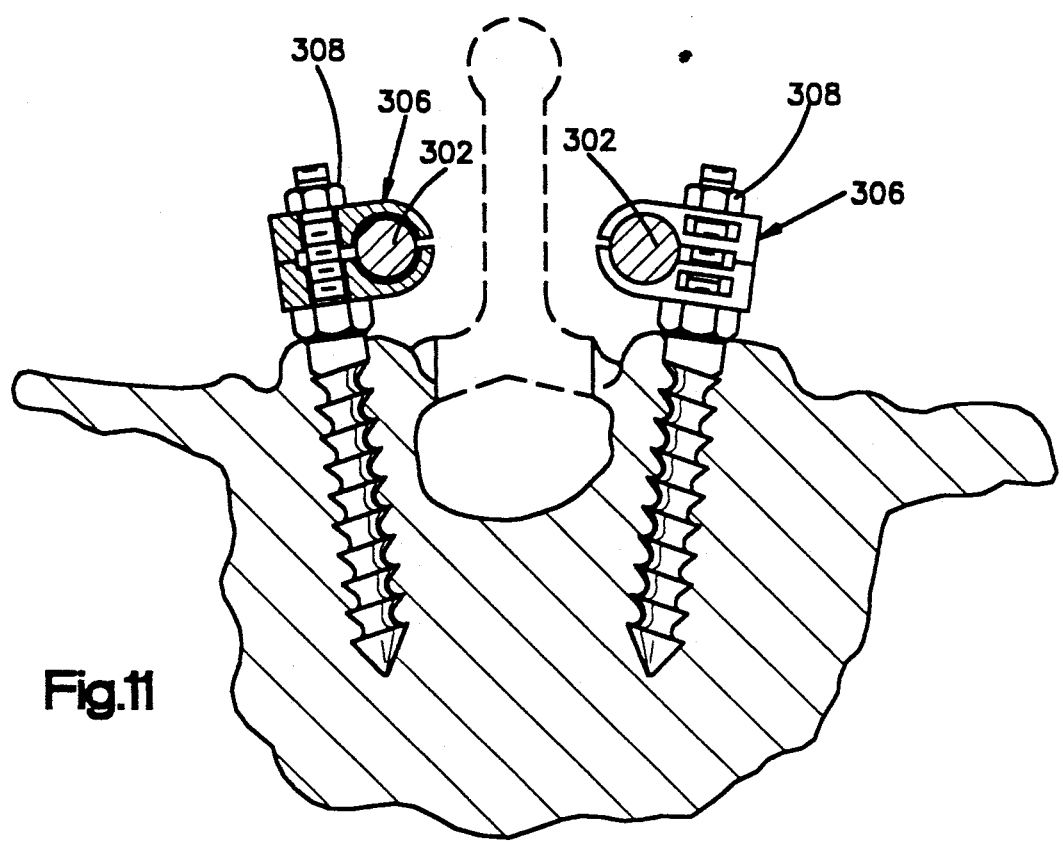
FIG. 11 is an enlarged cross sectional view of rods in FIG. 10 connected to a vertebra, taken approximately along line 11—11 in FIG. 10.
Figure 12:
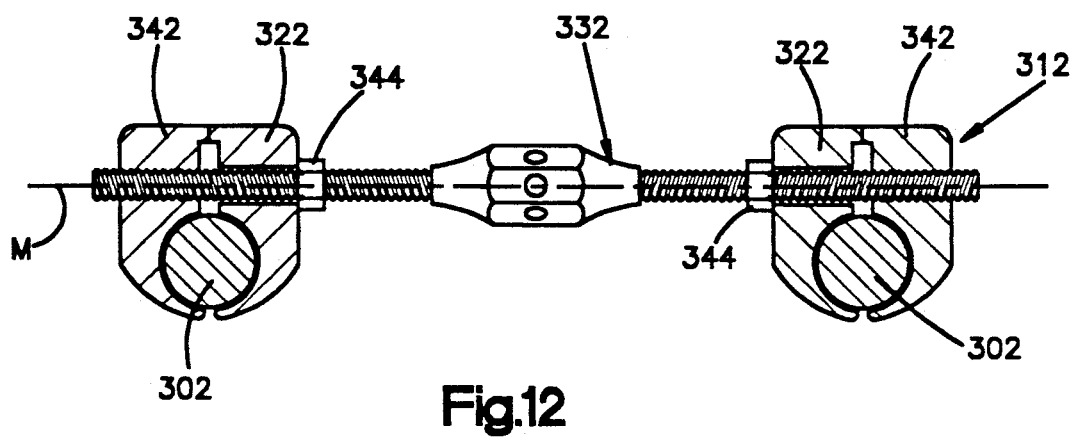
FIG. 12 is an enlarged cross sectional view of the transverse connector in FIG. 10 interconnecting rods, taken approximately along line 12—12 in FIG. 10.

Another embodiment of the transverse connector of the present invention is illustrated in FIGS. 10 and 12. A pair of known elongate rods 302 are connected with vertebrae V of the spinal column C by hooks 304 and/or by clamps 306 and fasteners 308, as illustrated in FIG. 11. Transverse connectors 312, similar to the transverse connectors 202, described above and illustrated in FIGS. 6 and 7, interconnects the rods 302.

Each rod 302 has a circular cross section taken in a plane extending perpendicular to the longitudinal central axis of the rod 302 and is bendable to conform to a desired curvature of the spinal column C. After the rods 302 are connected to the vertebrae V of the spinal column C, the transverse connector 312 is supported so the outer clamp halves 342 are located outside of the rods 302. The member 332 is rotated about its longitudinal central axis M in a direction so the outer clamp halves 342 move toward rods 302 to engage a portion of a respective rod 302. The inner clamp halves 322 are moved toward the rods 302 by tightening nuts 344 to clamp the rods and block relative movement between the rods.

Figure 13:
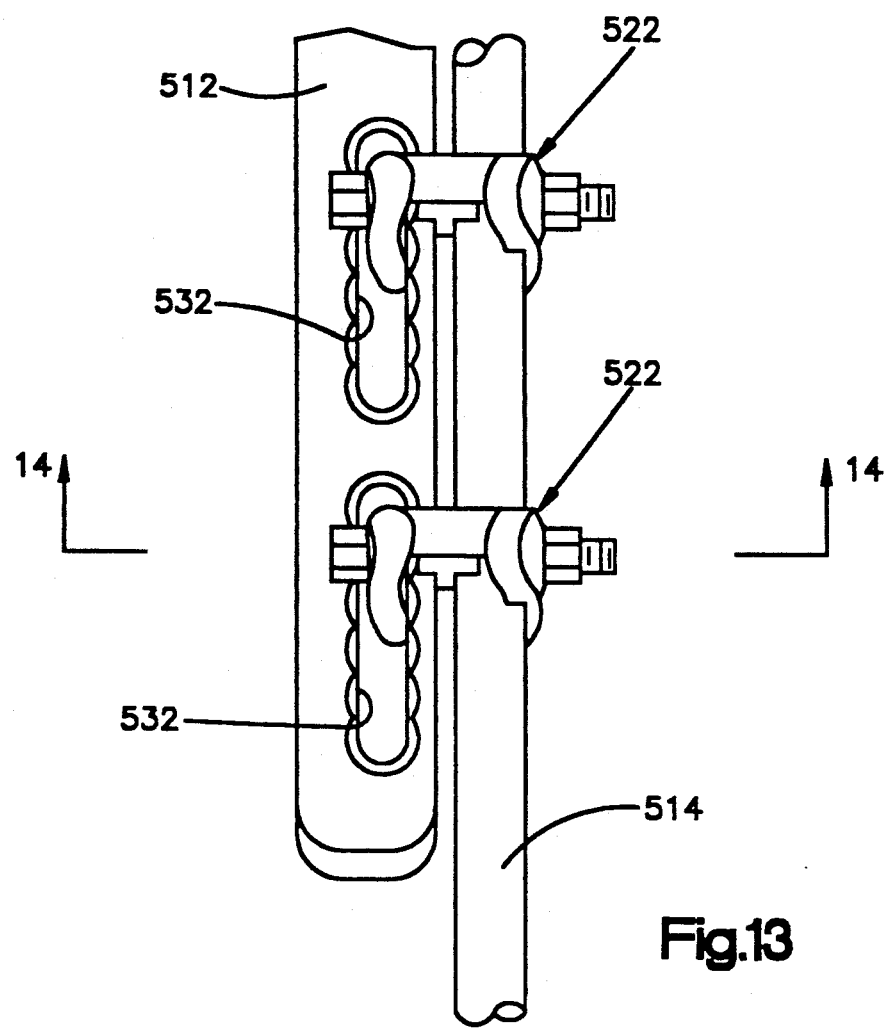
Figure 14:
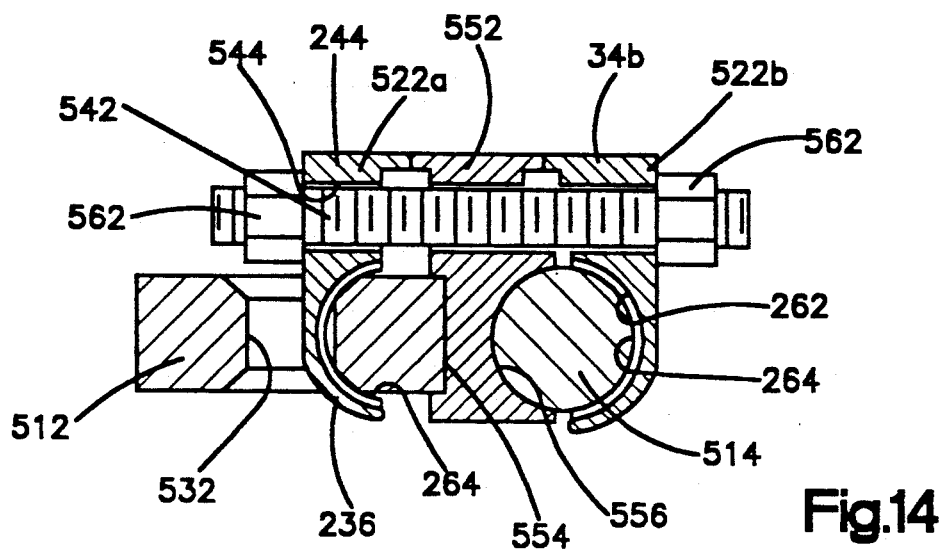
FIG. 14 is an enlarged cross sectional view of the transverse connector in FIG. 13, taken approximately along line 14—14 in FIG. 13.

An alternate use for the clamps is illustrated in FIGS. 13 and 14. When it is desired to connect a pair of parallel extending corrective members to one another the clamps, described above, may be used. Clamps 522 are used at axially spaced locations along the members. One of the members is a known spine plate 512 as described in U.S. Pat. No. 4,611,581 and the other of the members is a rod 514.

Each of the clamps 522 (FIG. 13) includes a clamp half 522a in which the body portion 236 is inserted through an opening 532 in the spine plate 512. A threaded rod 542 is received through the opening 544 in the connector portion 244 of the clamp half 522a. An intermediate member 552 having a bore 554 is also received on the threaded rod 542. The intermediate member 552 has a rectangular opening 554 for receiving a portion of the spine plate 512 and an arcuate opening 556 identical to arcuate surface 264 for receiving a portion of the rod 514. Another clamp half 522b is received on the threaded rod 542 and a portion of the rod 514 is received in the arcuate recess 262 of the clamp half 522b. Each of the clamp halves 522a, 522b have axially spaced arcuate surfaces 264 in the recesses 262 which engage the respective members 512, 514 at axially spaced locations. A nut 562 is threaded on the threaded rod 542 to press the clamp halves 522a, 522b toward one another against the intermediate member 552 so the plate 512 and rod 514 are connected together and maintained spaced apart.

Figure 15:
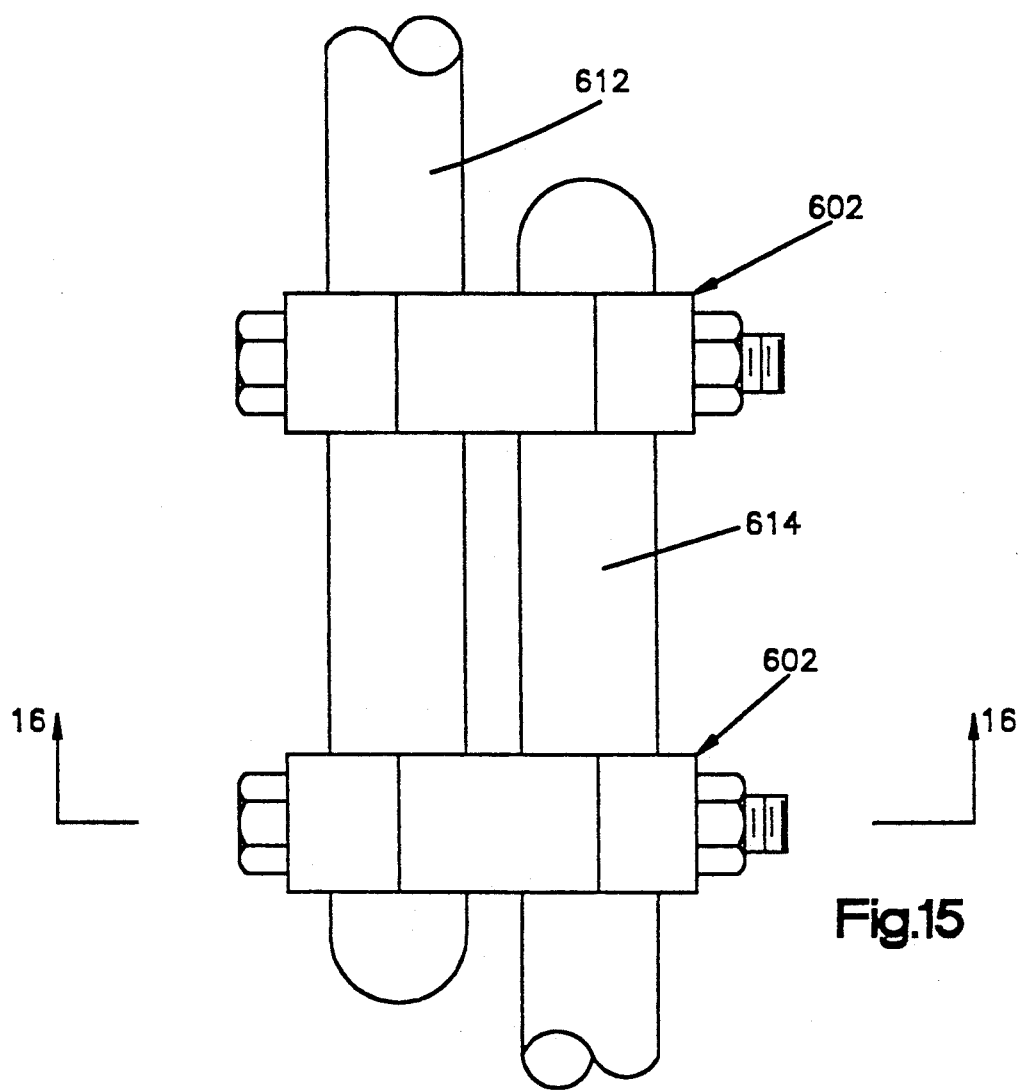
Figure 16:
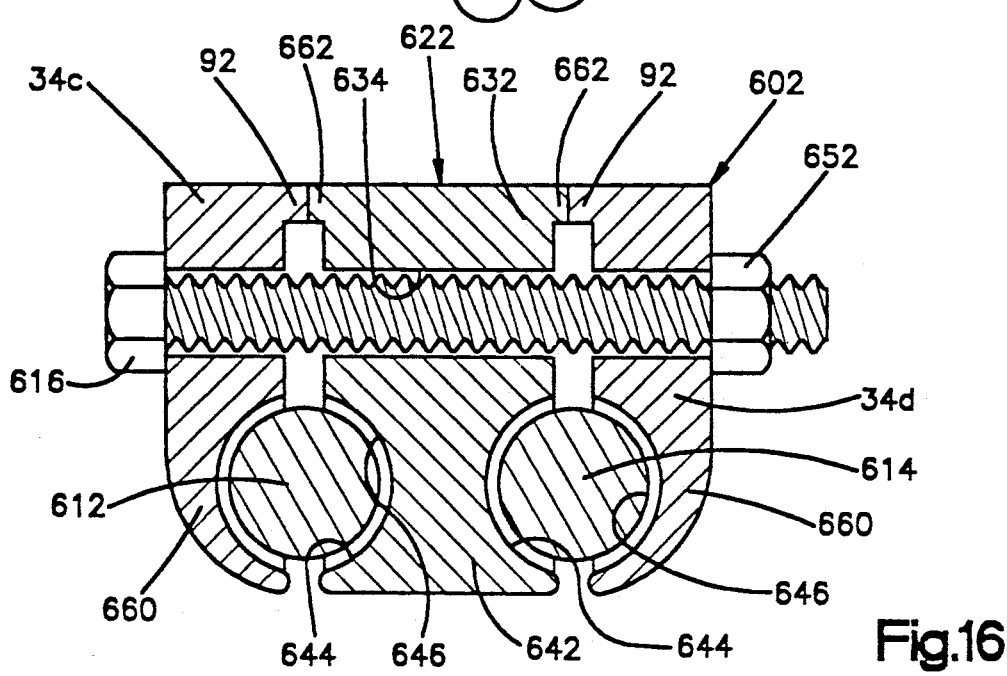
FIG. 16 is an enlarged cross sectional view of the transverse connector in FIG. 15, taken approximately along line 16—16 in FIG. 15.

Another use for the clamps for connecting members together is illustrated in FIGS. 15 and 16. A pair of clamps 602 connect two bendable spine rods 612, 614 together. Such clamps 602 are used when a broken spine rod is repaired by bridging the break in the rod or when two axially extending spine rods 612, 614 are to be connected together as illustrated in FIG. 15. Each clamp assembly 602 includes a pair of clamp halves 34c and 34d, as described above, which are received on a threaded rod 616.

An intermediate clamp portion 622 is located between the clamp halves 34c, 34d. The intermediate clamp portion 622 is located between the rods 612, 614 and spaces the rods apart a predetermined distance. The intermediate clamp portion 622 includes a connector portion 632 with an opening 634 for receiving the threaded rod 616. The intermediate clamp portion has a body portion 642 fixed to the connector portion 632 with a pair of oppositely facing arcuate recesses 644. Each of the arcuate recesses 644 has a pair of axially spaced apart arcuate surfaces 646 for engaging a portion of a rod 612 or 614.

The clamp halves 34c, 34d are located on opposite sides of the intermediate clamp portion 622. A nut 652 is threaded onto the threaded rod 616 to engage one of the clamp halves 34d and press the clamp halves 34c, 34d toward one another and against the intermediate clamp portion 632. Spacer portions 92 and 662 extending from each of the clamp halves 34c, 34d and from the intermediate clamp portion 622, respectively, engage to pivot the body portions 660 of the clamp halves 34c, 34d toward one another to clamp the rods 612, 614 against the intermediate clamp portion 622 as the nuts 652 are tightened.

Figure 17:
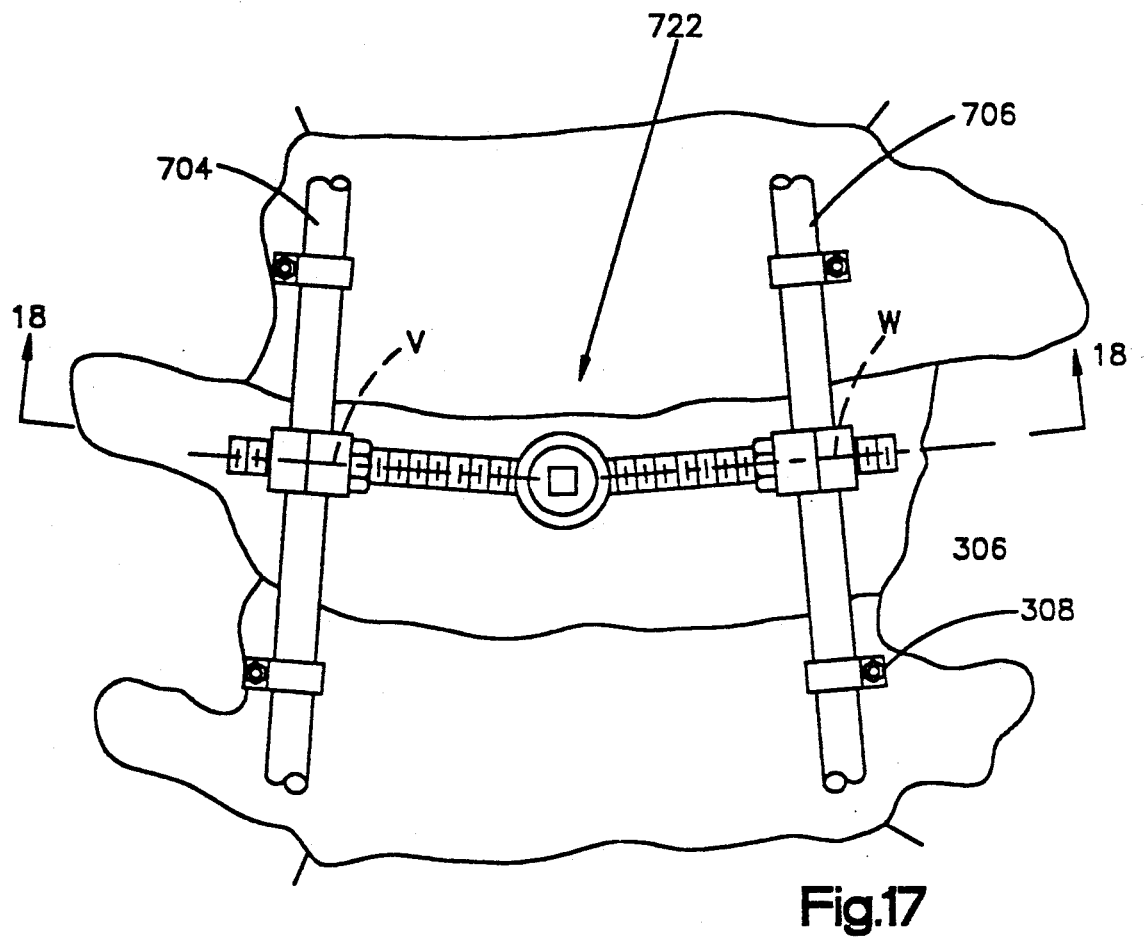
Figure 18:
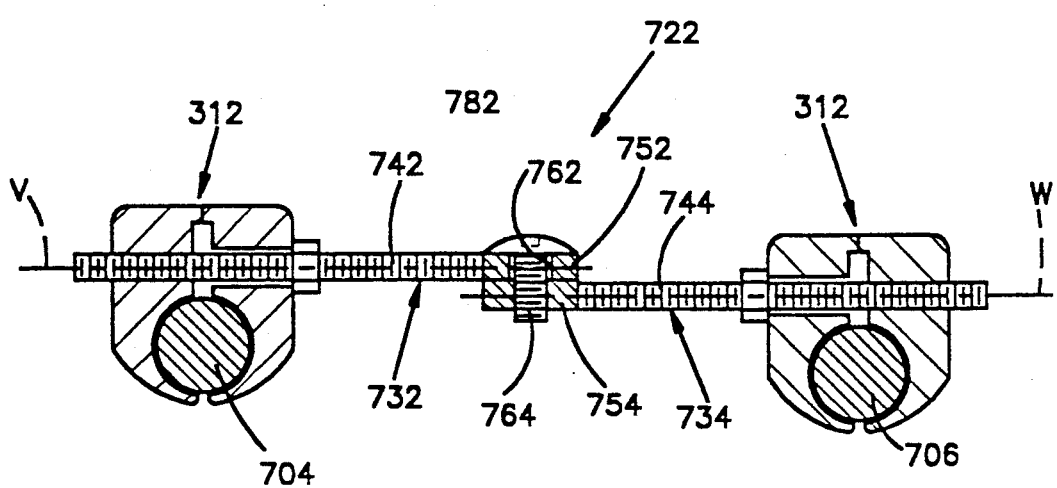
FIG. 18 is an enlarged cross sectional view of the transverse connector in FIG. 17, taken approximately along line 18—18 in FIG. 17.

Another embodiment of the transverse connector of the present invention is illustrated in FIGS. 17 and 18. A pair of know elongate spine rods 704 and 706 are connected with vertebrae V of the spinal column by clamps 306 and fasteners 308. An articulated transverse connector 722 interconnects the spine rods 704 and 706. It will be apparent that in this embodiment of the present invention, the spine rods 704 and 706 are located on the spinal column in a skewed relationship The transverse connector 722 accommodates such a skewed relationship without the need for permanently bending any of the components.

The transverse connector 722 (FIG. 18) includes a pair of threaded members or eyebolts 732, 734. Each of the eyebolts have a threaded portion 742, 744, respectively. Each of the threaded portions 742, 744 receive a clamp 312 as illustrated in FIG. 12 and described above. Each of the connecting members 732, 734 also include an axial end portion 752, 754, respectively. The axial end portion 752 has an opening 762 extending therethrough. The axial end portion 754 has a threaded opening 764 extending therethrough.

A fastener 782 is received through the opening 762 in the axial end portion 752 of the connecting member 732. The fastener has an end portion which threadingly engages in the threaded opening 764 of the axial end portion 754 of the connecting member 734. When the fastener 782 is tightened, the axial end portions 752, 754 are pressed together to prevent any movement between the connecting members 732, 734.

In order to accommodate the skewed relationship between the spine rods 704, 706, the connecting members 732, 734 may be located so that their longitudinal central axes may be disposed at an angle relative to one another as illustrated in FIG. 17. To permit this angular relationship, the clamps 312 are attached to the spine rods 704, 706 so that the axial end portions are located in an overlapping relationship. This may occur because the connecting members 734, 732 extend generally perpendicular from the respective spine rods 704, 706. The fastener is then inserted through the axial end portion 752 and threaded into the opening 764 in axial end portion 754. The fastener 782 is then tightened to maintain the spine rods in a spaced apart relationship. Thus, the transverse connector 722 is used without bending any of the components.

While FIGS. 1, 4, 6 and 10 illustrate by way of example two transverse connectors, in some cases only one transverse connector may be required and in other cases more than two may be required. Further, from the above description of a preferred embodiment of the invention, those skilled in the art will perceive improvements, changes and modifications. Such improvements, changes and modifications within the skill of the art are intended to be covered by the appended claims.

Having described a preferred embodiment of the invention, we claim:

1. An apparatus comprising:
   a pair of spine plates each of which includes a plurality of openings for receiving a fastener to connect said spine plate to a vertebra;
   a member extendable between said spine plates in a direction transverse to the axes of the openings in said spine plates;
   first attaching means for connecting a first portion of said member with one of said spine plates and second attaching means for connecting a second portion of said member with the other of said spine plates; and
   means for enabling a change in the location of said first and second attaching means along said member to enable said member to interconnect said spine plates spaced different distances apart.

2. The apparatus set forth in claim 1 wherein each of said spine plates is elongate and the openings in each of said spine plates are elongate and extend in a direction substantially parallel to and along a longitudinal central axis of said spine plate.

3. The apparatus set forth in claim 2 wherein said member comprises an elongate plate including surface mean defining an elongate opening extending in a direction substantially parallel to a longitudinal central axis of said elongate plate and each of said first and second attaching means comprises a fastener including a portion extendable through the opening in said elongate plate and one of the openings in one of said spine plates.

4. The apparatus set forth in claim 3 wherein said means for enabling a change in the location of said first and second attaching means comprises said surface means defining the elongate opening in said elongate plate and said portion of said fastener being locatable at different positions along the length of the opening in said elongate plate.

5. The apparatus set forth in claim 2 wherein said member comprises an elongate rod including externally threaded axial end portions and each of said first and second attaching means comprises a clamp connectable with a threaded end portion of said rod, said clamp including a first portion receivable in one of the openings in one of said spine plates and a second portion cooperating with said first portion to apply a clamping force to a portion of said one spine plate.

6. The apparatus set forth in claim 5 further including surface means on said first and second portions of said clamp defining a rectangular opening for clamping around a portion of the said spine plate having a rectangular cross section to block relative pivotal movement between said clamp and said one spine plate.

7. The apparatus set forth in claim 6 further including a pair of internally threaded members receivable on a threaded end portion of said rod at opposite sides of said clamp to block movement of said clamp along said rod and to move said first and second portions of said clamp toward one another to apply the clamping force to said portion of said one spine plate when said threaded members are tightened on said rod in a direction toward one another.

8. The apparatus set forth in claim 5 wherein said threaded end portions of said rod are threaded in opposite directions and further including a drive portion on said rod located intermediate said threaded end portions for receiving a force to rotate said rod about its longitudinal central axis, surface means defining an internally threaded opening in said first portion of said clamp for threaded engagement with one of the threaded end portions of said rod to cause said first portion of said clamp to move axially along said rod in response to rotation of said rod about its longitudinal central axis, surface means defining an opening in said second portion of said clamp for receiving said one threaded end portion of said rod and an internally threaded member receivable on said one threaded end portion of said rod on a side of said second portion of said clamp axially opposite said first portion of said clamp to move said second portion of said clamp toward said first portion of said clamp during tightening of said threaded member on said rod.

9. An apparatus for interconnecting a pair of spine plates each of which have a plurality of openings for receiving a fastener to connect the spine plate to a vertebra, said apparatus comprising:
   a member extendable between the spine plates in a direction transverse to the axes of the openings in the spine plates;
   first attaching means for connecting a first portion of said member with one of the spine plates and second attaching means for connecting a second portion of said member with the other of the spine plates, each of said first and second attaching means including a first portion receivable in an opening in one of the spine plates and a second portion cooperating with said first portion to apply a clamping force to a portion of the one spine plate; and
   means for enabling a change in the location of said first and second attaching means along said member to enable said member to interconnect spine plates spaced different distances apart.

10. The apparatus set forth in claim 9 wherein said member comprises an elongate plate and further including surface means defining an elongate opening extending through said elongate plate and in a direction substantially parallel to the longitudinal central axis of said elongate plate and wherein said first portion of each of said first and second attaching means comprises a fastener including a portion extendable through the opening in said elongate plate and one of the openings in one of the spine plates, and said second portion of each of said attaching means comprises another portion of said fastener engageable with the one spine plate.

11. The apparatus set forth in claim 10 wherein said means for enabling a change in the location of said first and second attaching means comprises said elongate opening, said portion of said fastener receivable in the elongate opening in said elongate plate and said portion of said fastener being locatable at different positions along the length of the opening in the elongate plate.

12. The apparatus set forth in claim 9 wherein said member comprises an elongate rod including externally threaded axial end portions and each of said first and second attaching means comprises a clamp connectable with a respective threaded end portion of said rod.

13. The apparatus set forth in claim 12 further including surface means on said first and second portions of said clamp defining a rectangular opening for clamping around a portion of the one spine plate having a rectangular cross section to block relative pivotal movement between the one spine plate and said clamp.

14. The apparatus set forth in claim 12 further including a pair of internally threaded members receivable on a threaded end portion of said rod at opposite sides of said clamp to block movement of said clamp along said rod and to move said first and second portions toward one another to apply the clamping force to said portion of said spine plate when the threaded members are tightened on said rod in a direction toward one another.

15. The apparatus set forth in claim 12 wherein said threaded end portions of said rod are threaded in opposite directions and further including a drive portion on said rod located intermediate said threaded end portions for receiving a force to rotate said rod about its longitudinal central axis, surface means defining an internally threaded opening in said first portion of said clamp for threaded engagement with one of the threaded end portions of said rod to cause said first portion of said clamp to move axially along said rod in response to rotation of said rod about its longitudinal central axis, surface means defining an opening in said second portion of said clamp for receiving said one threaded end portion of said rod and an internally threaded member receivable on said one threaded end portion of said rod on a side of said second portion of said clamp axially opposite said first portion of said clamp to move said second portion of said clamp toward said first portion of said clamp during tightening of said threaded member on said rod.

16. An apparatus for interconnecting a pair of spine plates each of which have a plurality of openings for receiving a fastener to connect the spine plate to a vertebra, said apparatus comprising:
an elongate rod extendable between the spine plates and having threaded end portions;
a pair of clamps, each of said clamps being connectable with a respective threaded end portion of said rod and including a first portion receivable in one of the openings in one of the spine plates and a second portion cooperating with said first portion to apply a clamping force to a portion of the one spine plate; and
means for moving first portions of said clamps relatively toward one another in response to rotation of said rod about its longitudinal central axis in a first direction and for moving first portions of said clamps relatively away from one another in response to rotation of said rod about its longitudinal central axis in a second direction opposite the first direction to enable said rod to interconnect spine plates spaced different distances apart.

17. The apparatus set forth in claim 16 wherein said threaded end portions of said rod are threaded in opposite directions and further including a drive portion on said rod located intermediate said threaded end portions for receiving a force to rotate said rod about its longitudinal central axis, surface means defining an internally threaded opening in said first portion of said clamp for threaded engagement with one of the threaded end portions of said rod to cause said first portion of said clamp to move axially along said rod in response to rotation of said rod about its longitudinal central axis, surface means defining an opening in said second portion of said clamp for receiving said one threaded end portion of said rod and an internally threaded member receivable on said one threaded end portion of said rod on a side of said second portion of said clamp axially opposite said first portion of said clamp to move said second portion of said clamp toward said first portion of said clamp during tightening of said threaded member on said rod.

18. An apparatus for interconnecting a pair of elongate members each of which are connectable with vertebrae of a spinal column, said apparatus comprising:
an elongate rod extendable between the members in a direction transverse to the longitudinal central axes of the members and including threaded end portions;
a pair of clamps, each of said clamps being connectable with a respective threaded end portion of said rod and including a first portion and a second portion cooperating with said first portion to apply a clamping force to a portion of one of said members when said first and second portions are pressed together;
means for pressing together said first and second portions of each of said clamps; and
means for enabling a change in the location of each of said pair of clamps relative to each other along said rod to enable said rod to interconnect the members spaced different distances apart.

19. The apparatus set forth in claim 18 further including means for moving said first portions of said clamps relatively toward one another in response to rotation of said rod about its longitudinal central axis in a first direction and for moving said first portions of said clamps relatively away from one another in response to rotation of said rod about its longitudinal central axis in a second direction opposite the first direction.

20. The apparatus set forth in claim 19 wherein said threaded end portions of said rod are threaded in opposite directions and further including a drive portion on said rod located intermediate said threaded end portions for receiving a torque to rotate said rod about its longitudinal central axis, surface means defining an internally threaded opening in said first portion of said clamp for threaded engagement with one of the threaded end portions of said rod to cause said first portion of said clamp to move axially along said rod in response to rotation of said rod about its longitudinal central axis, surface means defining an opening in said second portion of said clamp for receiving said one threaded end portion of said rod and an internally threaded member receivable on said one threaded end portion of said rod on a side of said second portion of said clamp axially opposite said first portion of said clamp to move said second portion of said clamp toward said first portion of said clamp during tightening of said threaded member on said rod.

21. An apparatus for connecting a first member to a second member, said apparatus comprising:
an intermediate clamp portion including a first end portion and a second end portion having a pair of oppositely facing recesses;
a first clamp portion including a first end portion and a second end portion having a recess for cooperating with one of said recesses in said intermediate clamp portion to clamp a portion of the first member when said first clamp portion is pressed toward said intermediate clamp portion;
a second clamp portion including a first end portion and a second end portion having a recess for cooperating with the other of said recesses in said intermediate clamp portion to clamp a portion of the second member when said second clamp portion is pressed toward said intermediate clamp portions;
means for pressing said first and second clamp portions toward said intermediate clamp portions;
means for spacing apart said first end portions of said clamp portions and for pivoting said second end portions of said first and second clamp portions toward said second end portion of said intermediate clamp portion as said first and second clamp portions are pressed toward said intermediate clamp portion; and
means located in each of said recesses for engaging the first and second members at axially spaced locations.

22. The apparatus set forth in claim 21 wherein one of said recesses in said intermediate clamp portion is rectangular.

23. The apparatus set forth in claim 21 wherein said recesses in said intermediate clamp portion are arcuate.

24. An apparatus for interconnecting a pair of elongate members each of which are connectable with vertebrae of a spinal column, said apparatus comprising:
a first connecting member having an axial end portion and a longitudinal central axis;
first clamp means for attaching one of the pair of elongate members to said first connecting member;
a second connecting member having an axial end portion and a longitudinal central axis;
second clamp means for attaching the other one of the pair of elongate members to said second connecting member; and
joint means for connecting together said axial end portions of said first and second connecting members to enable said first and second connecting members to be positioned with said longitudinal central axes skewed relative to one another.

25. The apparatus set forth in claim 24 wherein said joint means for connecting together said axial end portions of said first and second connecting members comprises a fastener, said axial end portion of said first connecting member having an opening extending therethrough for receiving a portion of said fastener and said axial end portion of said second connecting member having a threaded opening for threaded engagement with said fastener to pres said axial end portions of said first and second connecting members together upon tightening said fastener.

* * * * *

UNITED STATES PATENT AND TRADEMARK OFFICE
CERTIFICATE OF CORRECTION

PATENT NO. : 5,084,049

DATED : January 28, 1992

INVENTOR(S) : Marc Asher, Walter E. Strippgen, Charles Heinig and William Carson.

It is certified that error appears in the above-identified patent and that said Letters Patent is hereby corrected as shown below:

Column 9, Line 53, Claim 3, change "mean" to --means--.

Column 14, Line 34, Claim 25, change "pres" to --press--.

Signed and Sealed this

Twenty-seventh Day of April, 1993

Attest:

MICHAEL K. KIRK

Attesting Officer

Acting Commissioner of Patents and Trademarks